United States Patent [19]

Lin

[11] Patent Number: 4,676,933

[45] Date of Patent: Jun. 30, 1987

[54] METHOD FOR PURIFICATION OF AMIDO ACIDS

[75] Inventor: Jiang-Jen Lin, Round Rock, Tex.

[73] Assignee: Texaco Inc., White Plains, Tex.

[21] Appl. No.: 920,826

[22] Filed: Oct. 20, 1986

[51] Int. Cl.$^4$ .................... C07C 102/00; C07C 103/27
[52] U.S. Cl. ........................................ 260/404; 502/29
[58] Field of Search ......................................... 260/404

[56] References Cited

U.S. PATENT DOCUMENTS

| | | |
|---|---|---|
| 2,167,931 | 8/1939 | McAllister et al. .................. 260/404 |
| 2,542,766 | 2/1951 | Gresham .............................. 260/404 |
| 2,760,977 | 8/1956 | Fever et al. .......................... 260/404 |
| 3,006,934 | 10/1961 | Dieckelmann ...................... 260/404 |
| 3,264,281 | 8/1966 | Applewhite et al. ................ 260/404 |
| 3,927,048 | 12/1975 | Duranleau et al. .................. 260/404 |

FOREIGN PATENT DOCUMENTS

| | | | |
|---|---|---|---|
| 1064728 | 4/1967 | United Kingdom | ................ 260/404 |
| 1074693 | 7/1967 | United Kingdom | ................ 260/404 |
| 1081159 | 3/1984 | U.S.S.R. | ............................. 260/404 |

OTHER PUBLICATIONS

Vogel, "Practical Organic Chemistry", 3rd ed. (1957), pp. 122-125.

*Primary Examiner*—J. E. Evans
*Attorney, Agent, or Firm*—Jack H. Park; Kenneth R. Priem; Cynthia L. Kendrick

[57] ABSTRACT

A method for purification of $C_{12}$-$C_{16}$ amido acids prepared from $C_{10}$-$C_{14}$ amido acids is disclosed. The amido acids are purified by dissolving the crude product in organic alcohol solvent and chloroform at a temperature between room temperature and about 60° C. and about atmospheric pressure. Then the solution is filtered, cooled and allowed to recrystallize. This method is effective for removing the Rh and Co bimetallic catalysts.

6 Claims, No Drawings

METHOD FOR PURIFICATION OF AMIDO ACIDS

FIELD OF THE INVENTION

This invention relates to the purification of amido acids prepared by rhodium-cobalt catalyzed hydroformylation/amidocarbonylation of $C_{10}$–$C_{14}$ olefins.

More particularly this invention uses a mixed organic solvent comprising ethanol and chloroform in combination with water for the recrystallization of $C_{12}$–$C_{16}$ amido acids to remove contamination of Rh and Co catalysts.

BACKGROUND OF THE INVENTION

Various methods have been disclosed in the art for the synthesis of amido acids by hydroformylation/amidocarbonylation.

For example, Applicant's copending U.S. patent application Ser. No. 06/720,248 discloses a process for preparation of amido acids from alpha olefins, acetamide and syngas using a bimetallic rhodium-cobalt catalyst.

In processes such as these it is often difficult to obtain products in pure form. In addition some of the expensive catalysts are often lost in the process and metal contamination of the product usually occurs to some degree.

It would be an advance in the art to devise a method for purifying amido acids prepared from the Rh—Co catalyzed hydroformylation/amidocarbonylation of $C_{10}$–$C_{14}$ olefins wherein there is a great reduction in the amount of metal contamination from cobalt and rhodium.

SUMMARY OF THE INVENTION

This invention concerns a method for purifying solid amido acids prepared by rhodium-cobalt catalyzed hydroformylation/amidocarbonylation of $C_{10}$–$C_{14}$ olefins which comprises isolating the crude product by filtration, dissolving the crude product in an organic solvent comprising ethanol and a cosolvent comprising chloroform, and recrystallizing the product with water at a temperature from room temperature to 60° C. and at atmospheric pressure.

The process allows for a product which has much greater purity. In Example V the metal contamination from cobalt in the $C_{12}$-amido acid product was reduced from 967 ppm to 15 ppm and the metal contamination from rhodium was reduced from 29 ppm to <0.5 ppm.

DETAILED DESCRIPTION OF THE INVENTION

In the narrower and more preferred practice of this invention the purification of solid amido acids prepared by rhodium-cobalt catalyzed hydroformylation of $C_{10}$–$C_{14}$ olefins is disclosed by a process which comprises isolating the crude product by filtration, dissolving the crude product in an organic solvent comprising ethanol and a cosolvent consisting of chloroform and recrystallizing the product with water at a temperature from room temperature to 60° C. and at atmospheric pressure.

The $C_{12}$–$C_{16}$ amido acid products are recrystallized in pure form with the presence of much fewer parts per million of metal contaminants.

The solvent system suitable for the practice of this invention comprises an organic solvent, a cosolvent and water.

The mixed organic solvent provides the following important advantages to isolate the crude products.
1. The purity of the product is upgraded.
2. Contamination of cobalt metal can be reduced from as much as 967 ppm to 15 ppm and contamination of rhodium metal can be reduced from as much as 29 ppm to <0.5 ppm.
3. It is possible to recover more of the expensive catalyst.

The solvent suitable in this purification method may be chosen from a variety of organic solvents. The organic solvent compound should be an alcohol solvent. Suitable compounds include methanol, propanol, 2-(2-ethoxylethoxyl)ethanol and ethanol. The preferred organic solvent is ethanol.

The organic cosolvent may take many different forms. It may be an ethyl acetate, p-dioxane, chloroform, acetonitrile or methylene chloride. Typical examples include p-dioxane, acetonitrile, ethyl acetate and triethylamine and chloroform, although all of these compounds besides chloroform were tested and shown not as effective as chloroform cosolvent mixed with ethanol. In the case of triethylamine, the product failed to recrystallize from the EtOH/Et$_3$N/H$_2$O solvent.

The quantity of organic solvent to cosolvent to be used in purifying the product may vary. The process is conducted in the presence of a quantity of organic solvent sufficient to dissolve the product. The cosolvent concentration can range from about 10% to about 80% based on the total weight of the mixed organic solvent mixture.

Operating conditions may vary over a wide range. The reaction temperature may vary from room temperature to about 60° C. The preferred temperature is from about 40° C. to about 60° C. The pressure should be about atmospheric. The use of a temperature from 40° C. to 60° C. indicates as shown in Examples I–V that the ethanol is preferably hot. The $C_{12}$–$C_{16}$ amido acid product is dissolved in this hot solution.

The following examples illustrate the process of the invention. The crude product was isolated by filtration and obtained as a light gray solid contaminated with different degrees of Rh and Co content. The different examples illustrate the use of various organic solvents and water to recrystallize and purify $C_{12}$–$C_{14}$ amido acids. It is to be understood, however, that the examples are given in the way of illustration and are not to be regarded as limiting the invention in any way.

EXAMPLE I

Example I demonstrates the synthesis of alkyl-amido acid by Rh—Co catalyst (Copending U.S. patent application Ser. No. 06/720,248). This is the type reaction by which one obtains the crude product which is purified in the instant process.

The typical experimental procedures for synthesis of alkyl-amido acids from α-olefin, acetamide and syngas are illustrated by the following example.

To a glass-lined pressure reactor was charged HRh(CO)(PPh$_3$)$_3$ (0.046 g), Co$_2$(CO)$_8$ (0.34 g), acetamide (3.0 g), 1-tetradecene (9.8 g) and ethyl acetate (10.0 g). The reactor was sealed and pressured with CO—H$_2$ (1:1 molar ratio). At the conditions of 2000 psi, 100° C. for 4 hours. At room temperature, the recovered materials (25.4 g) contained some crystalline solid after filtration, the crude $C_{16}$-amido acid (13.8 g) was obtained. The yield to this compound was estimated to be cr. 89%. The crude product contained some rhodium and cobalt catalyst.

EXAMPLE II

A portion of $C_{16}$-amido acid crude product (63.0 g), light pink solid, contaminated with Co (6240 ppm) and Rh (34 ppm) was dissolved in hot ethanol. The hot solution was quickly filtered to remove trace amounts of insoluble material. The filtrate was allowed to cool to room temperature. Some crystalline solid appeared and was obtained by filtration. The analysis of solid (ca. 20 g) product showed the contamination of 1670 ppm cobalt and 41 ppm rhodium. The filtrate was added to an excess amount of water, and white solid was precipitated immediately. The filtration procedure recovered a second solid product (ca. 38 g) with analysis of cobalt 538 ppm and rhodium 1.2 ppm.

The comparison of metal contamination of two solid materials showed the effectiveness of water coprecipitation.

EXAMPLE III

A portion of $C_{12}$-amido acid crude product (21 g, grey solid, contaminated with Co 253 ppm and Rh<1 ppm) was dissolved in hot ethanol (ca. 50° C.). The hot solution was filtered to remove trace amounts of insoluble material. The filtrate was cooled to room temperature. The crystalline solid appeared (ca. 12 g); the liquid was decanted into 100 cc of deionized water. The white solid was collected and dried to afford a 9.0 g product with contamination of Co 43 ppm and Rh<1 ppm.

EXAMPLE IV

Procedures similar to those described above were applied to a portion of $C_{14}$-amido acid (ca. 20 g, grey solid, cobalt 1910 ppm, rhodium 45 ppm). After recrystallization from ethanol and water, the final product contained cobalt 291 ppm and rhodium 16 ppm.

EXAMPLE V

A portion of crude $C_{16}$-amido acid (40 g, Co 252 ppm and Rh 3.3 ppm) was recrystallized from ethanol/water solution using the previous procedure to afford 37.0 g white solid with metal contamination of 180 ppm Co and 1.3 ppm Rh.

EXAMPLE VI

A portion of crude $C_{12}$-amido acid (10.0 g, Co 967 ppm, Rh 29 ppm) was dissolved in 20 g chloroform and 20 g ethanol at "hot" temperature. The hot solution was filtered to remove insoluble material and poured into an excess amount of deionized water. The white precipitate was collected by filtration (ca. 7.0 g). The analyses showed metal contamination of 15 ppm cobalt and <0.5 ppm rhodium. The highly effective method of recrystallization using $EtOH/CHCl_3/H_2O$ cosolvents was demonstrated.

Other organic cosolvents, including p-dioxane, 2-(2-ethoxyethoxy)ethanol, acetonitrile, methanol, ethyl acetate and triethylamine in combination with water were tested and showed not as effective as the $EtOH/CHCl_3$ cosolvent. In the case of triethylamine, the product failed to recrystallize from $EtOH/Et_3N/H_2O$ solvent.

What is claimed is:

1. A method for purification of $C_{12}$–$C_{16}$ amido acids prepared from Rh—Co catalyzed hydroformylation/carbonylation of $C_{10}$–$C_{14}$ olefins which comprises
   (A) isolating the amido acid product by filtration,
   (B) dissolving the crude product in an organic solvent consisting of an alcohol solvent from the group consisting of methanol and ethanol and a cosolvent from the group consisting of ethyl acetate, p-dioxane and and chloroform,
   (C) precipitating the product by diluting with water at a temperature between room temperature and about 60° C. and at about atmospheric pressure,
   whereby the process upgrades product purity, reduces metal contamination in the product and allows more efficient recovery of expensive catalyst.

2. The process of claim 1 wherein the organic solvent is ethanol.

3. The process of claim 1 wherein the cosolvent is chloroform.

4. The process of claim 1 wherein ethanol, chloroform and water are used in a ratio of about 1:1:10 to 2:1:100 based on the total weight of the solvent system.

5. The process of claim 2 wherein the ethanol is heated before the crude product is dissolved therein.

6. The process of claim 1 wherein the temperature is from 25° C. to 60° C.

* * * * *